United States Patent [19]

Mahler

[11] 4,454,763

[45] Jun. 19, 1984

[54] ROTARY ULTRASONIC SCAN HEAD INCLUDING FLUID DRIVE

[75] Inventor: George D. Mahler, Federal Way, Wash.

[73] Assignee: Washington Research Foundation, Seattle, Wash.

[21] Appl. No.: 407,568

[22] Filed: Aug. 12, 1982

[51] Int. Cl.³ .......................................... G01N 29/04
[52] U.S. Cl. ........................................ 73/639; 73/641
[58] Field of Search ................. 73/633, 639, 620, 641; 128/660

[56] References Cited

U.S. PATENT DOCUMENTS

| | | | |
|---|---|---|---|
| 4,034,744 | 7/1977 | Goldberg | 128/660 |
| 4,102,204 | 7/1978 | Kretz | 73/639 |
| 4,149,419 | 4/1979 | Connell et al. | 73/639 |
| 4,228,687 | 10/1980 | Fraser | 73/641 |

OTHER PUBLICATIONS

Barber et al., "Duplex Scanner II: For Simultaneous Imaging of Artery Tissues and Flow", 1974 Ultrasonics Symposium Proceedings, (1974).
Barber et al., "Ultrasonic Duplex Echo-Doppler Scanner", IEEE Transactions on Biomedical Engineering, (1974).

*Primary Examiner*—Anthony V. Ciarlante
*Attorney, Agent, or Firm*—Christensen, O'Connor, Johnson & Kindness

[57] ABSTRACT

A rotary ultrasonic scan head includes a housing 10 consisting of generally symmetrical housing portions 10A and 10B having respective mating surfaces 14 and 16 that abut when the housing portions are assembled. A cavity is defined within the housing by recesses 18, 27, 34 and 38 in housing portion 10A and by complementary recesses 20, 28, 36 and 40 in housing portion 10B, by boot 50 disposed on the housing portions in assembly, and by pressure-compensating diaphragm member 42 disposed within the housing portions in assembly. A rotor 12 including a plurality of ultrasonic transducers 22, an impeller 24, and an optically encoded member 26 is supported for rotation within this cavity. An acoustic coupling and driving fluid is supplied to and withdrawn from the cavity through fluid inlet bore 68 and fluid outlet bore 70 in housing portion 10A, with the fluid entering the cavity being directed at impeller 24. A rotary transformer couples electrical signals between housing portion 10A and the rotor, and a plurality of reed switches within the rotor and permanent magnets 94 and 96 disposed in housing portion 10A commutate these electrical signals so that each transducer is enabled only when that transducer is traversing a desired sector. Fiber-optic bundles 108 and 110 disposed in housing portion 10B optically couple member 26 to external light sources and detectors so that the relative angular position, speed of rotation, and direction of rotation of the rotor can be determined.

40 Claims, 8 Drawing Figures

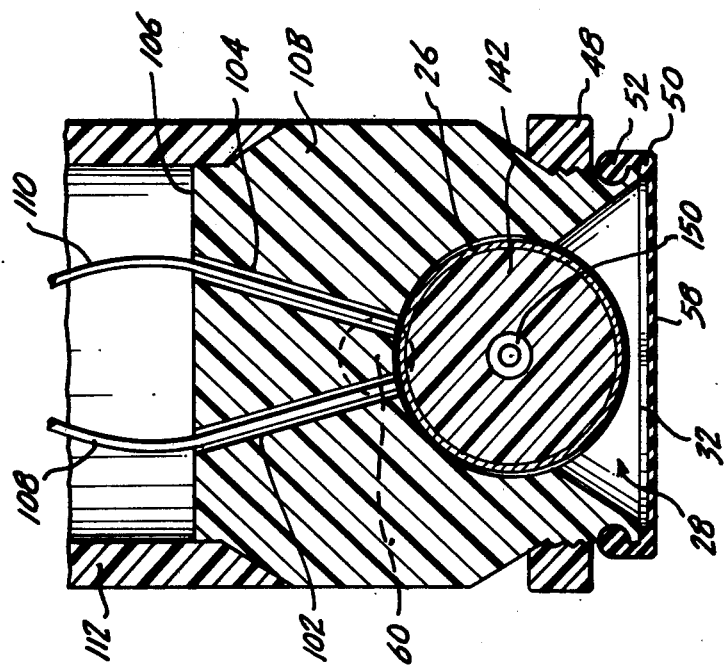
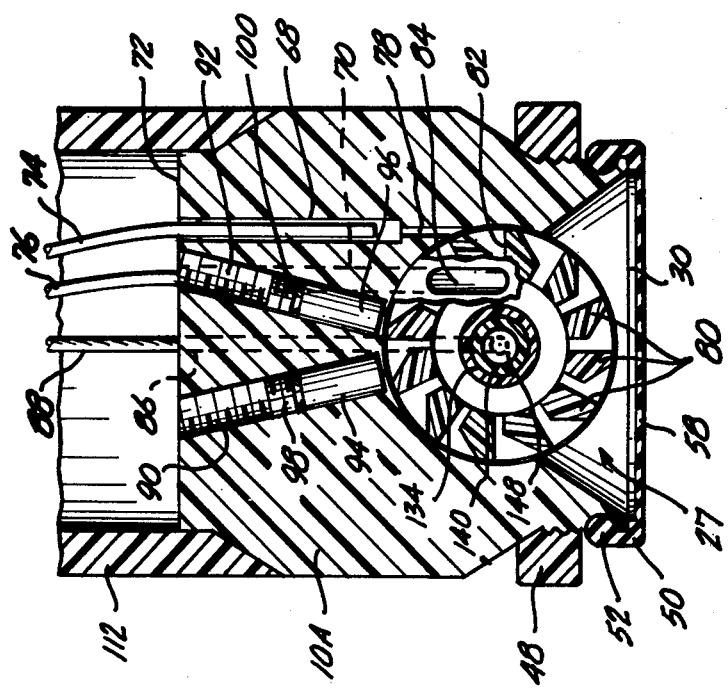

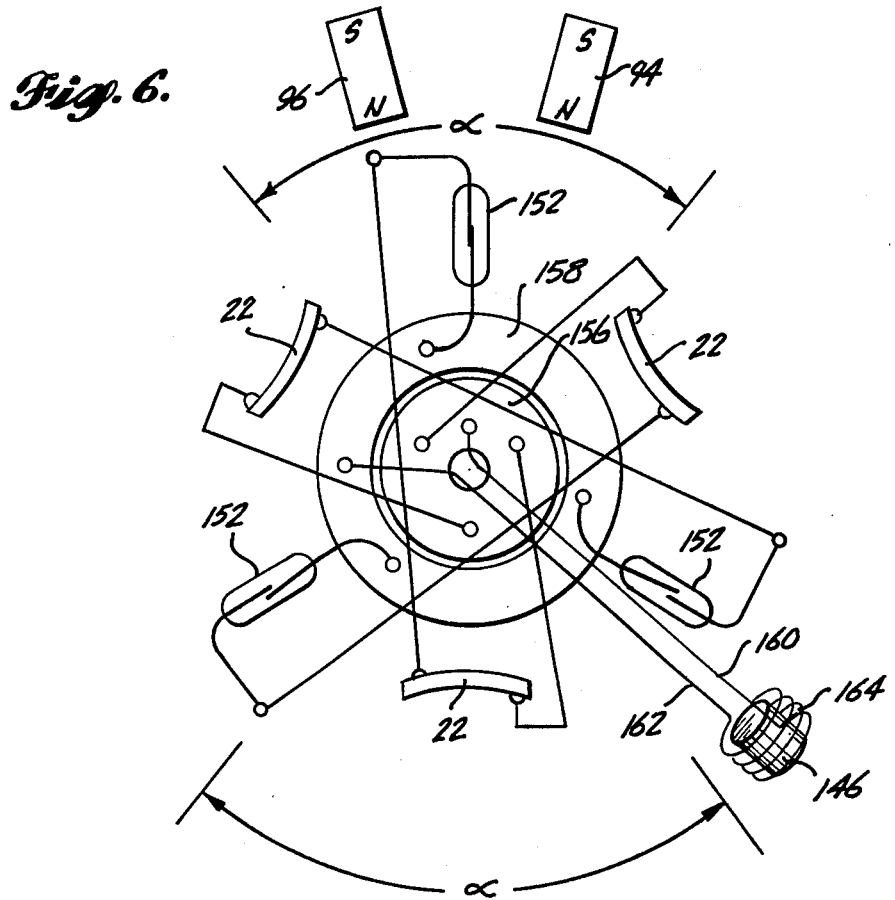
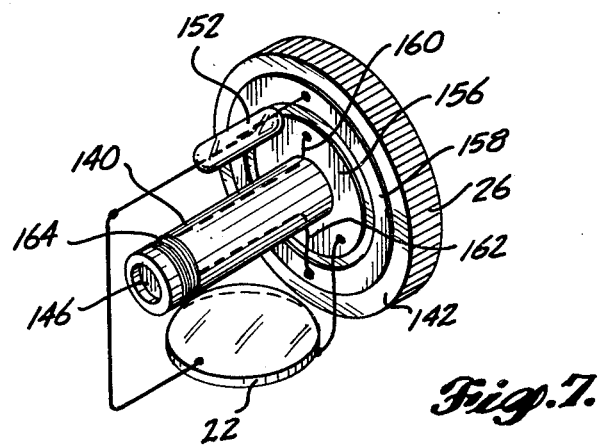

ROTARY ULTRASONIC SCAN HEAD INCLUDING FLUID DRIVE

FIELD OF THE INVENTION

This invention generally relates to rotary ultrasonic scan heads of the type including a rotor supporting at least one ultrasonic transducer that is selectively actuated during rotation of the rotor to effect a mechanical sector scan of an object with ultrasonic energy, and more particularly to such a scan head in which the rotor is driven by fluid supplied to the scan head.

BACKGROUND OF THE INVENTION

Ultrasonic imaging systems are known to the prior art for providing real-time, cross-sectional images of human cardiac, abdominal and peripheral vascular structure that are of substantial diagnostic value. While various types of image formats have been provided, one of the more useful image formats from a diagnostic standpoint is the two-dimensional sector image that comprises an image of those body tissues located within a substantial planar sector. To provide such a sector image, the ultrasonic imaging system includes a scanner, a scan converter, and a display. The great majority of scanners in use today provide a mechanical scan of the sector and include a hand-held scan head that is maintained in contact with the skin of the body during use. The scan head contains a rotor that supports at least one ultrasonic transducer. During rotation of the rotor, the transducer is enabled for ultrasonic energy transmission and reception while the transducer is traversing a desired sectorial angle. When enabled, the transducer is caused to transmit ultrasonic energy and receive returns of the transmitted ultrasonic energy at each of a plurality of incremental angular positions (or scan lines) in the sector. The output signal from the transducer, representing the returns of transmitted ultrasonic energy, is in analog form and is referenced to a polar coordinate system. In order that the output signal may be visually displayed, in real-time, by a conventional video display whose scan is based on a Cartesian coordinate system and whose scanning rate may differ from that of the scanner, the output signal is buffered and converted to Cartesian coordinates by the scan converter before being supplied to the display.

Now considering the structure of a typical prior art scan head in more detail, the scan head includes a housing that defines a cavity in which the rotor is supported for rotation. The cavity is filled with an acoustic coupling fluid (such as oil or water) and is closed by a thin acoustic window that is either attached to or integral with the scan head housing. A plurality of ultrasonic transducers are disposed at equal angular intervals about the periphery of the rotor so as to be capable of ultrasonic energy transmission and reception in directions transverse to the rotor axis of rotation. The ultrasonic energy passes through the acoustic coupling fluid, the acoustic window, and an acoustic jelly that covers the acoustic window and that contacts the skin of the body. Provision is made for coupling electrical signals to and from the transducers on the rotor and for commutating these electrical signals so that each transducer is enabled only over the desired sector, e.g., during the time that the transducer is substantially aligned with the acoustic window. In order to drive the rotor, an electrical drive motor (typically a DC motor) is mounted within the housing. The motor shaft (or a shaft coupled thereto) extends into the cavity and is coupled to the rotor shaft, either directly or indirectly through a gear arrangement. To prevent leakage of the acoustic coupling fluid from the cavity into that portion of the housing containing the electrical drive motor, a seal (such as an O-ring seal) is disposed about the motor shaft. Finally, the rotor speed of rotation and angular position are sensed by an encoded member carried by the motor shaft and by an adjacent and stationary detector mounted in the housing.

Despite their widespread acceptance, the rotary ultrasonic scan heads known to the prior art have certain disadvantages. The leakage of acoustic coupling fluid from the cavity into the portion of the housing containing the electrical drive motor remains a problem and it has proven very difficult to provide an adequate, reliable, and long-lasting seal about the motor shaft to prevent such leakage. Although it is theoretically possible to provide a leakproof seal about the motor shaft, the resultant increase in friction makes such a seal unfeasible for hand-held scan heads in which the output torque available from the electrical drive motor is limited by the requirement that the electrical drive motor have a weight and size suitable for use in a hand-held housing. Although the prior art scan heads have been the subject of considerable development which has reduced their weight and size and increased their reliability, the scan heads remain expensive to manufacture due to the large number of separate mechanical components therein and often experience failure after an extensive period of use due to mechanical wear of these components. Due to the weight and size of the electrical drive motor and its drive train, the scan heads become tiring to manipulate after an extensive period of continuous use. Since the scan heads include an electrical drive motor to which electrical power is supplied, the scan heads oftentimes cannot be used in circumstances in which potential electrical or explosive hazards must be eliminated.

Yet another disadvantage results in the fact that the electrical drive motor and its drive train exhibit vibration during operation. Although this vibration may degrade the sector image developed by the scan head, it is most critical in the situation in which a fixed Doppler transducer is mounted on or integral with the scan head for the purpose of obtaining a duplex image containing both real-time position and velocity information. In this situation, it is essential that the scan head be vibrationless to optimize any signals from the Doppler transducer.

Due to their construction, the prior art scan heads cannot be modified or serviced by the user. As an example, the user may wish to change the operating characteristics of the scan head, such as the frequency, aperture, or focal length of the transducers. The prior art scan heads have not been designed to permit the user to disassemble the housing, replace the transducers and the rotor, and reassemble the housing so that the cavity is filled with acoustic coupling fluid and is devoid of air. If different operating characteristics of the scan head are desired, the user accordingly must either purchase a new scan head having the desired operating characteristics or return the existing scan head to the manufacturer for modification.

SUMMARY OF THE INVENTION

The rotary ultrasonic scan head of the present invention comprises:

a housing;

a rotor supported within the housing for rotation, the rotor having a predetermined axis of rotation and including at least one ultrasonic transducer that is disposed so as to be capable of ultrasonic energy transmission and reception in directions transverse to the axis of rotation; and, a fluid drive motor disposed within the housing and operatively associated with the rotor for rotating the rotor about its axis in response to the supply of a fluid to the fluid drive motor.

In a preferred embodiment, the fluid drive motor includes: a cavity defined within the housing; an impeller disposed within the cavity and forming part of the rotor; and fluid inlet means and fluid outlet means disposed in the housing and being respectively adapted to conduct fluid to and from the cavity, the fluid inlet means being disposed so as to direct the fluid conducted therethrough at the impeller. Preferably, the entirety of the rotor is disposed within the cavity so that the fluid circulated therethrough also serves as an acoustic coupling fluid for the ultrasonic energy transmitted and received by the ultrasonic transducer. Preferably, the housing includes first and second, separable housing portions having corresponding mating surfaces that abut in assembly, and the scan head further comprises means for maintaining the first and second housing portions in assembly. The cavity is defined by at least one recess extending into the first housing portion from its mating surface and at least one complementary recess extending into the second housing portion from its mating surface.

In combination with the scan head of the preferred embodiment, a fluid drive system may be used that comprises a source of a fluid suitable for rotating the rotor and for coupling ultrasonic energy to and from the ultrasonic transducer included in the rotor, and means for recirculating the fluid through the source and the scan head, by conducting fluid from the source to the fluid inlet means and by conducting fluid from the fluid outlet means to the source. Preferably, the fluid is water, and the scan head further includes means disposed in the housing for bleeding air from the cavity as the fluid is recirculated.

BRIEF DESCRIPTION OF THE DRAWINGS

The invention can best be understood by reference to the following portion of the specification, taken in conjunction with the accompanying drawings in which:

FIG. 3 is a cross-sectional view of the scan head taken along the lines 3—3 in FIG. 2;

FIG. 4 is a cross-sectional view of the scan head taken along the lines 4—4 in FIG. 2;

FIG. 6 is a schematic diagram of the electrical components of the rotor;

FIG. 7 is a pictorial view of the rotor in partial assembly; and,

DESCRIPTION OF A PREFERRED EMBODIMENT

Figure 1:
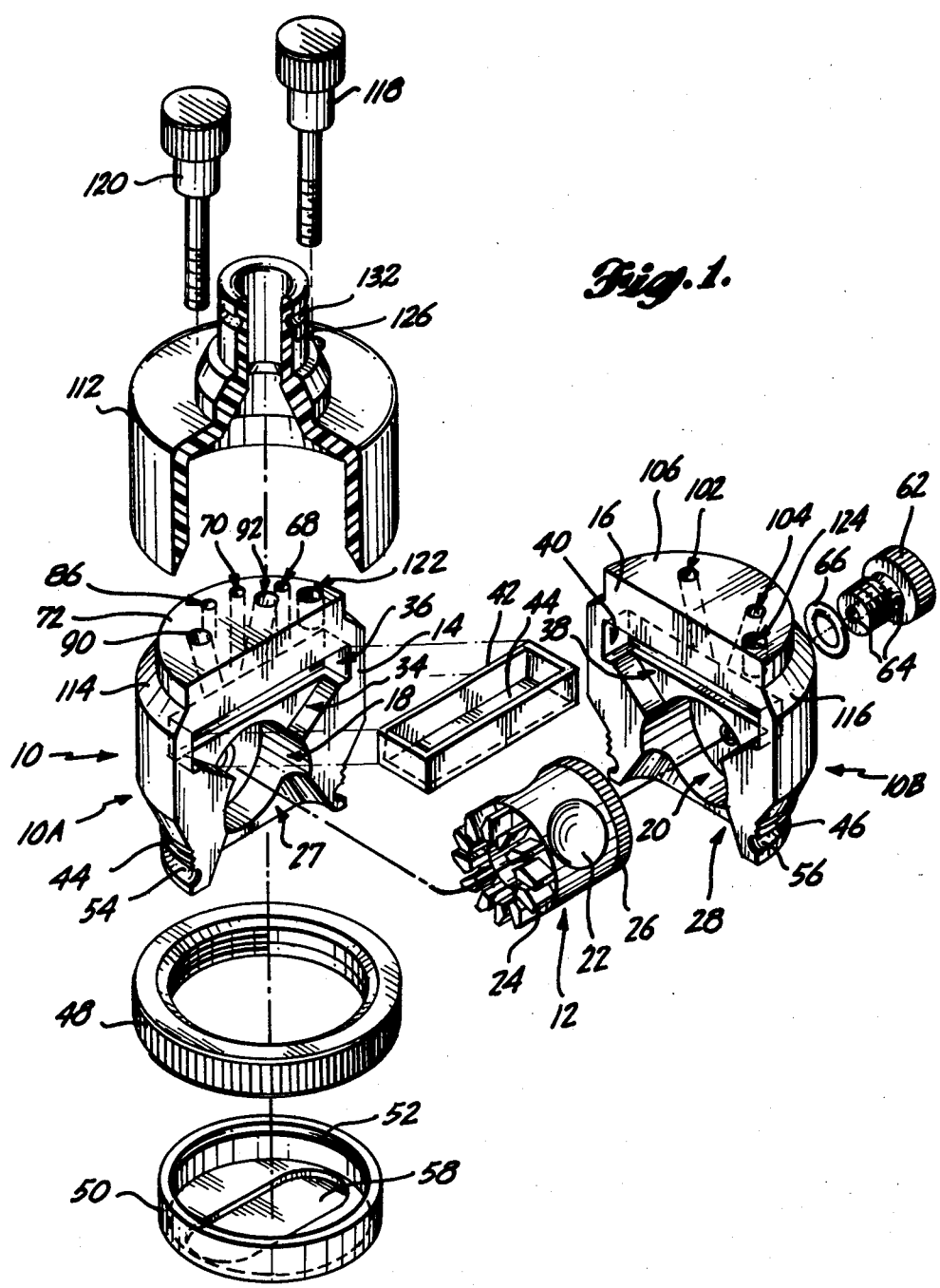
FIG. 1 is an exploded, pictorial view of the scan head of the present invention.
Figure 2:
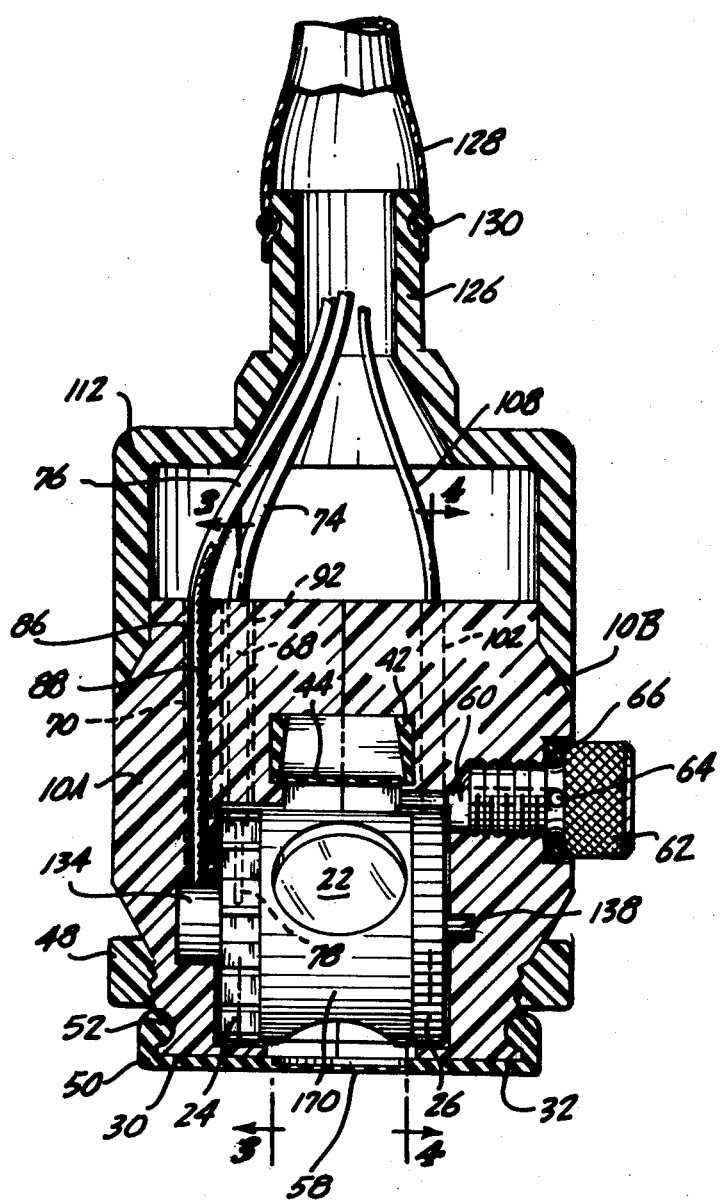
FIG. 2 is a cross-sectional view of the scan head in FIG. 1 in assembly.

Referring now to FIGS. 1 and 2, the major components of the scan head are a housing 10 comprising housing portions 10A and 10B and a rotor 12 supported for rotation within housing 10. Preferably, housing portions 10A and 10B are substantially symmetrical halves of a generally cylindrical body and have corresponding, substantially planar surfaces 14 and 16 which abut in assembly. A substantially cylindrical recess 18 extends from surface 14 into housing portion 10A, and a corresponding substantially cylindrical recess 20 extends from surface 16 into housing portion 10B. Rotor 12, which has a generally cylindrical shape, is received within recesses 18 and 20 in assembly and is supported for rotation by pivots supported in the floors of recesses 18 and 20 and by corresponding jeweled bearings supported at the respective ends of rotor 12.

Rotor 12 includes at least one and preferably a plurality of ultrasonic transducers 22, an impeller 24, and an optically encoded ring 26. Ultrasonic transducers 22 are preferably located at equal angular intervals about the axis of rotation of rotor 12 and are disposed so that each ultrasonic transducer 22 is capable of ultrasonic energy transmission and reception in directions transverse to that axis of rotation.

A second recess 27 extends from surface 14 into housing portion 10A and a second recess 28 extends from surface 16 into housing portion 10B. Second recess 27 communicates at its upper end with cylindrical recess 18, is open at its lower end defined by a bottom surface 30 of housing portion 10A, and tapers outwardly from recess 18 to bottom surface 30. In an identical manner, second recess 28 communicates at its upper end with cylindrical recess 20, is open at its lower end defined by a bottom surface 32 of housing portion 10B, and tapers outwardly from recess 20 to bottom surface 32. A third recess 34 and a fourth recess 36 extend from surface 14 into housing portion 10A, and a third recess 38 and a fourth recess 40 extend from surface 16 into housing portion 10B. Recesses 36 and 40 each have a substantially rectangular shape and receive in assembly a pressure-compensating diaphragm member 42, which is in the shape of a hollow rectangle of flexible material whose lower end is closed by an integral diaphragm 44. Recess 34 communicates at its lower end with cylindrical recess 18, communicates at its upper end with rectangular recess 36, and tapers outwardly from recess 18 to recess 36. Likewise, recess 38 communicates at its lower end with cylindrical recess 20, communicates at its upper end with rectangular recess 40, and tapers outwardly from recess 20 to recess 40.

In order to permit housing portions 10A and 10B, pressure-compensating diaphragm member 42, and rotor 12 to be assembled and disassembled, a rotatable collar 48 is provided that has internal threads engaging external threads 44 and 46 about the periphery of housing portions 10A and 10B adjacent bottom surfaces 30 and 32, respectively. In assembly, the lower ends of recesses 27 and 28 define a substantially oval aperture in the bottom surfaces 30 and 32 of housing portions 10A and 10B through which ultrasonic energy may be transmitted and received. This oval aperture is closed and sealed by a boot 50 of flexible material that is retained by the engagement of an integral, inwardly facing ring 52 with corresponding annular grooves 54 and 56 formed in the periphery of housing portions 10A and 10B immediately above respective bottom surfaces 30 and 32. The boot 50 also has defined therein a thin diaphragm or "acoustic window" 58 that has a substantially oval configuration complementary to that of the oval aperture defined by the lower ends of recesses 27 and 28 and that is substantially aligned with that oval aperture when boot 50 is assembled with housing portions 10A and 10B.

As will be appreciated from the foregoing description, the various recesses in housing portions 10A and 10B define a cavity in assembly within which rotor 12 is supported for rotation and which is bounded at its upper end by pressure-compensating diaphragm member 42 (and diaphragm 44 therein) and at its lower end by boot 50 (and acoustic window 58 therein). In the manner to be described hereinafter, this cavity is completely filled with an acoustic coupling fluid that facilitates the transmission and reception of ultrasonic energy by ultrasonic transducers 22 through acoustic window 58. During use, boot 50 is covered with an acoustic jelly and is pressed against the skin of a patient in proximity to the area to be scanned. The flexible material of boot 50 permits the scan head to closely conform to the adjacent skin surface but requires that pressure-compensating diaphragm member 42 be included in the scan head so that the fluid pressure within the cavity is not subjected to undue variations upon deflection of boot 50. In order that air may be removed from the cavity in the manner to be described hereinafter, a threaded bore 60 extends from the periphery of housing portion 10B to the floors of recesses 20 and 38. A threaded screw 62 having a bleed port 64 is received in bore 60 and an O-ring seal 66 carried by screw 62 seals bleed port 64 and bore 60 when screw 62 is completely received within bore 60.

One of the principal advantages of the invention arises from the fact that the acoustic coupling fluid is also used to drive the rotor. In this regard, and with additional reference to FIG. 3, impeller 24 is disposed within cylindrical recess 18 in assembly. A fluid inlet bore 68 and a fluid outlet bore 70 extend from a tap surface 72 of housing portion 10A to recess 18. A flexible fluid inlet tube 74 is fitted into and terminated within fluid inlet bore 68 and a flexible fluid outlet tube 76 is fitted into and terminated within fluid outlet bore 70. Tubes 74 and 76 are coupled to a fluid drive system as described hereinafter that functions to supply fluid under pressure through fluid inlet tube 74 and to withdraw fluid through fluid outlet tube 76.

At its lower end, fluid inlet bore 68 is provided with a reduced-diameter portion or nozzle 78 that enters the circumferential sidewall of cylindrical recess 18. Nozzle 78 is located so that a jet of fluid exits therefrom that is tangential to the circumferential sidewall of cylindrical recess 18 and that is intermediate the longitudinal or axial dimension of impeller 24 as best seen in FIG. 2. Impeller 24 is composed of a plurality of impeller blades 80 that are disposed at substantially equal angular intervals about the axis of rotaton of rotor 12. Each impeller blade 80 is provided with a substantially planar surface 82 that lies along a radius of rotor 12. The jet of fluid exiting from nozzle 78 impinges substantially normally on the blade surfaces 82 in succession so as to impart a rotational movement to rotor 12 (in a clockwise direction as viewed in FIG. 3). The fluid thus supplied also serves as an acoustic coupling fluid within the cavity as previously described.

At its lower end, fluid outlet bore 70 terminates in an aperture 84 disposed in the floor of cylindrical recess 18 at a location intermediate the center and the circumferential sidewall of recess 18. During an operation of the scan head in which rotation of rotor 12 is desired, the fluid drive system continuously circulates fluid through the cavity by supplying fluid through inlet tube 74, inlet bore 68, and nozzle 78 and by withdrawing the fluid through aperture 84, outlet bore 70, and outlet tube 76 in a manner so as to achieve a desired rotational speed of rotor 12 and so as to maintain the cavity completely filled with fluid.

Provision is also made for coupling electrical signals to and from ultrasonic transducers 22. To this end, a cable bore 86 extends from top surface 72 of housing portion 10A to a location approximately aligned with the center of cylindrical recess 18. A coaxial cable 88 is received within cable bore 86 and is electrically connected with a stationary portion of a rotary transformer (to be described in conjunction with FIG. 5) that functions to inductively couple electrical signals between housing portion 10A and rotor 12. In order to ensure that each transducer 22 is enabled only when the transducer is traversing a desired sector, the scan head includes a commutation device. Magnet bores 90 and 92 extend from top surface 72 of housing portion 10A along respective radii of cylindrical recess 18 to locations just above the circumferential sidewall of recess 18. Permanent magnets 94 and 96 are respectively received within bores 90 and 92 and retained therein by set screws 98 and 100 received in corresponding threaded portions of bores 90 and 92. As will be explained hereinafter, bores 90 and 92 are positioned and angularly disposed with respect to each other so that magnets 94 and 96 cause the actuation of each transducer 22 only when the transducer is traversing the desired sector.

Provision is also made to determine the angular position and speed of rotation of rotor 12. In this regard, and with additional reference to FIG. 4, optically encoded ring 26 is disposed in assembly within cylindrical recess 20 in housing portion 10B. Fiber-optic bores 102 and 104 extend along respective radii of cylindrical recess 20 from a top surface 106 of housing portion 10B to the circumferential sidewall of recess 20. Fiber-optic bundles 108 and 110 are received within and terminate in bores 102 and 104, respectively. Optically encoded ring 26 has a plurality of equal spaced areas disposed about its periphery, with each such area having a light reflectivity that differs from that of the remainder of ring 26. For example, these areas may be axially extending bars or gradations of low light reflectivity placed on a background of high light reflectivity. A light source and a light detector (not illustrated) are optically coupled to the end of each fiber-optic bundle 108 and 110. The movement of each area on optically encoded ring 26 past each fiber-optic bundle accordingly produces a pulse in the light detector output which can be used to determine the angular position and speed of rotation of rotor 12. Preferably, the angular position and speed of rotation are detected at two angularly spaced locations as illustrated in FIG. 4 in order to improve the accuracy and precision of those measurements and to permit the direction of rotation of rotor 12 to be determined by phase comparison of the light detector outputs.

The scan head is completed by a cylindrical cap 112 whose circumference is substantially identical to that of housing portions 10A and 10B in assembly. With particular reference to FIG. 1, cap 112 abuts corresponding shoulders 114 and 116 formed in housing portions 10A and 10B and is retained by screws 118 and 120 received in corresponding threaded apertures 122 and 124 extending into housing portions 10A and 10B from top surfaces 72 and 106, respectively. Cap 112 includes a central, hollow projection 126 through which fluid inlet tube 74, fluid outlet tube 76, cable 88, and fiber-optic bundles 108 and 110 pass. A flexible sheath 128, that is retained on projection 126 by the engagement of a snap ring 130 and an annular groove 132 on the periphery of projection 126, serves to form the tubes, cable, and fiber-optic bundles into a single bundle that extends to the fluid drive system to be described hereinafter and to the remaining electrical components of the scanner.

Housing portions 10A and 10B, collar 48 and cap 112 (reference FIG. 1) preferably are fabricated by molding, drilling and machining a suitable rigid plastic material (such as Delrin TM), and pressure-compensating diaphragm member 42 and boot 50 preferably are fabricated by molding a suitable flexible plastic material (such as Silastic TM).

Figure 5:
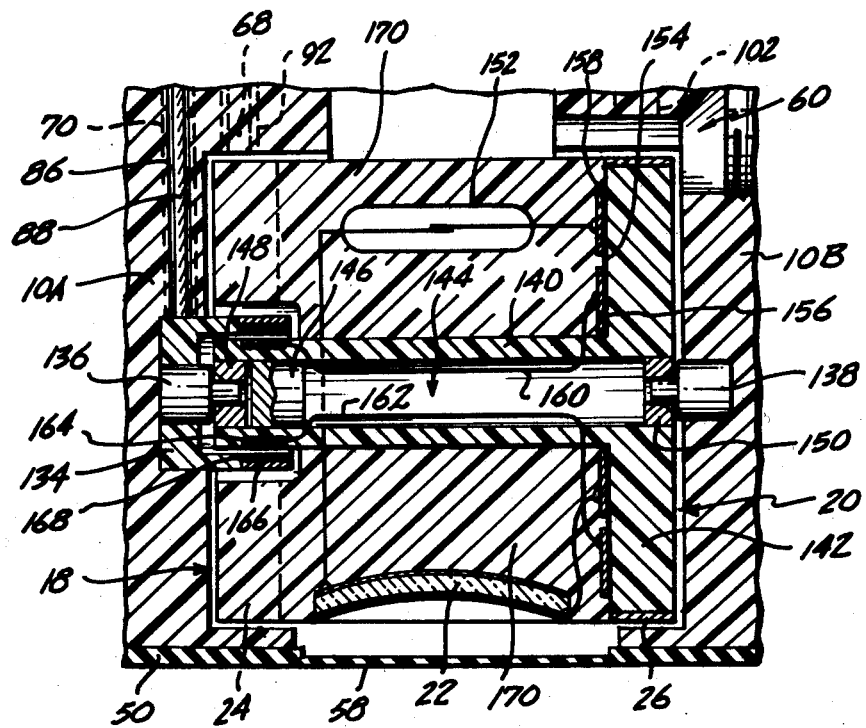
FIG. 5 is a cross-sectional view of a rotor forming part of the scan head.

To understand the structure and method of construction of rotor 12, the manner in which rotor 12 is supported for rotation, the manner in which electrical signals are coupled to and from rotor 12, and the manner in which transducers 22 are selectively actuated to effect a sector scan, reference should be made additionally to FIGS. 5, 6 and 7. A small cylindrical recess is centrally located in the floor of cylindrical recess 18 in housing portion 10A and a bushing 134 is fitted therein. Bushing 134 is provided with a central aperture in which is fitted a pivot 136. A small cylindrical recess is also centrally located in the floor of cylindrical recess 20 in housing portion 10B, and a pivot 138 is fitted therein. When housing portions 10A and 10B are assembled as previously described, pivots 136 and 138 are aligned so as to define an axis of rotation for rotor 12. Rotor 12 includes a cylindrical mandrel 140 and an enlarged disc 142 disposed at one end of mandrel 140 and integral therewith. An axial bore 144 extends through mandrel 140 and disc 142. A ferrite slug 146 and a jeweled bearing 148 are fitted in that order in the end of bore 144 away from disc 142, and a jeweled bearing 150 is fitted into the end of bore 144 proximate disc 142. In assembly, jeweled bearing 148 rides on pivot 136 and jeweled bearing 150 rides on pivot 138 so as to support rotor 12 for rotation.

In the preferred embodiment, rotor 12 includes three ultrasonic transducers 22 and three reed switches 152 with each reed switch being associated with a corresponding one of the ultrasonic transducers. The ultrasonic transducers and reed switches are each disposed at equal 120° degrees angular intervals about the axis of rotation of rotor 12, with each transducer diametrically opposing its associated reed switch. A printed circuit board 154 is affixed to disc 142 and has located thereon an inner conductive ring 156 and an outer conductive ring 158. One lead of each ultrasonic transducer 22 is soldered to inner conductive ring 156 and the other lead of each ultrasonic transducer 22 is soldered (either directly or through an intervening lead) to one lead of its associated reed switch 152 whose other lead is soldered to outer conductive ring 158. A lead 160 is soldered to inner conductive ring 156 and a lead 162 is soldered to outer conductive ring 158. Leads 160 and 162 pass into and through axial bore 144 in mandrel 140 and are connected to respective ends of a winding 164 that is disposed about the periphery of mandrel 140 so as to substantially surround slug 146. As can be seen in FIG. 5, a cylindrical ferrite sleeve 166 is affixed to the end of bushing 134 and a winding 168 is disposed within sleeve 166. The ends of winding 168 are connected (by means not illustrated) to the conductors of coaxial cable 88 going to the remaining portion of the scanner. In assembly, winding 164 is disposed in close proximity to winding 168. Accordingly, slug 146, winding 164, sleeve 166 and winding 168 comprise a rotary transformer that functions to inductively couple electrical signals between rotor 12 and housing portion 10A, and, more specifically, between inner and outer conductive rings 156 and 158 and the leads of coaxial cable 88.

Referring specifically to FIG. 6, each reed switch 152 is normally open so that the electrical circuit from outer conductive ring 158 to inner conductive ring 156 through its associated transducer 22 is broken. As rotor 12 is rotated, one and only one of the reed switches 152 is closed as that reed switch passes by permanent magnets 94 and 96 to accordingly complete the electrical circuit between outer conductive ring 158 and inner conductive ring 156 through its associated transducer 22. Due to the described structure of the scan head, each transducer 22 accordingly is enabled only when that transducer is moving in proximity to the acoustic window. The relative angular location of magnets 94 and 96 determines the angular interval α over which each reed switch 152 is closed and its associated transducer 22 is enabled and the angle α is accordingly the sectorial angle of the sector scan. As can be appreciated, the maximum sectorial angle for a scan head whose rotor includes three ultrasonic transducers is 120 degrees. However, the actual sectorial angle is preferably less than the maximum sectorial angle (e.g., 80 degrees) to ensure that only one reed switch is closed and only one transducer is enabled at any given point in time.

In constructing rotor 12, the mandrel 140 and disc 142 are first molded from a rigid plastic material (such as Delrin TM). Winding 164 is then wound around the end of mandrel 140 away from disc 142 and leads 160 and 162 are pulled through bore 144 and brought out through small radial apertures in mandrel 140 adjacent disc 142. The printed circuit board 154, having been previously fabricated, is fitted over mandrel 140 and secured to disc 142 by an appropriate adhesive and leads 160 and 162 are soldered to inner and outer conductive rings 156 and 158, respectively. Slug 146 is then fitted into the end of bore 144 away from disc 142 and secured by a suitable adhesive. The plurality of transducers 22 and reed switches 152 are assembled with the orientation previously described and the leads thereof are soldered to each other and to inner and outer conductive rings 156 and 158. The resultant assembly is then placed into a jig and mold into which is poured a suitable resinous material (such as an epoxy resin) which, when cured, forms impeller 24 and the remaining body 170 of rotor 12 between impeller 24 and disc 142. During this molding operation, it is important that the mold be completely filled with the resinous material so that air is not entrapped so as to form voids in body 170 that might adversely affect the performance of ultrasonic transducers 22. After curing, the assembly is removed from the mold and optically encoded ring 26 is fitted over the periphery of disc 142 and secured thereto by a suitable adhesive. For ease of manufacture, optically encoded ring 26 is preferably of a metallic material on which areas of differing light reflectivity have been formed by engraving or etching. Rotor 12 is completed by fitting jeweled bearings 148 and 150 into respective ends of bore 144 and securing those bearings by a suitable adhesive.

In the preferred embodiment, the resinous material used to form impeller 24 and body 170 of rotor 12 does not cover any of the ultrasonic transducers 22, inasmuch as each of the transducers is a focused type having a concave surface for the transmission and reception of ultrasonic energy that faces radially outwardly in assembly. However, a nonfocused-type of transducer may also be used and focusing may be provided by mounting a separate cylindrical focusing lens adjacent the transmitting and receiving surface of each transducer or by molding such a lens from the same resinous material that is used to form impeller 24 and body 170.

Figure 8:
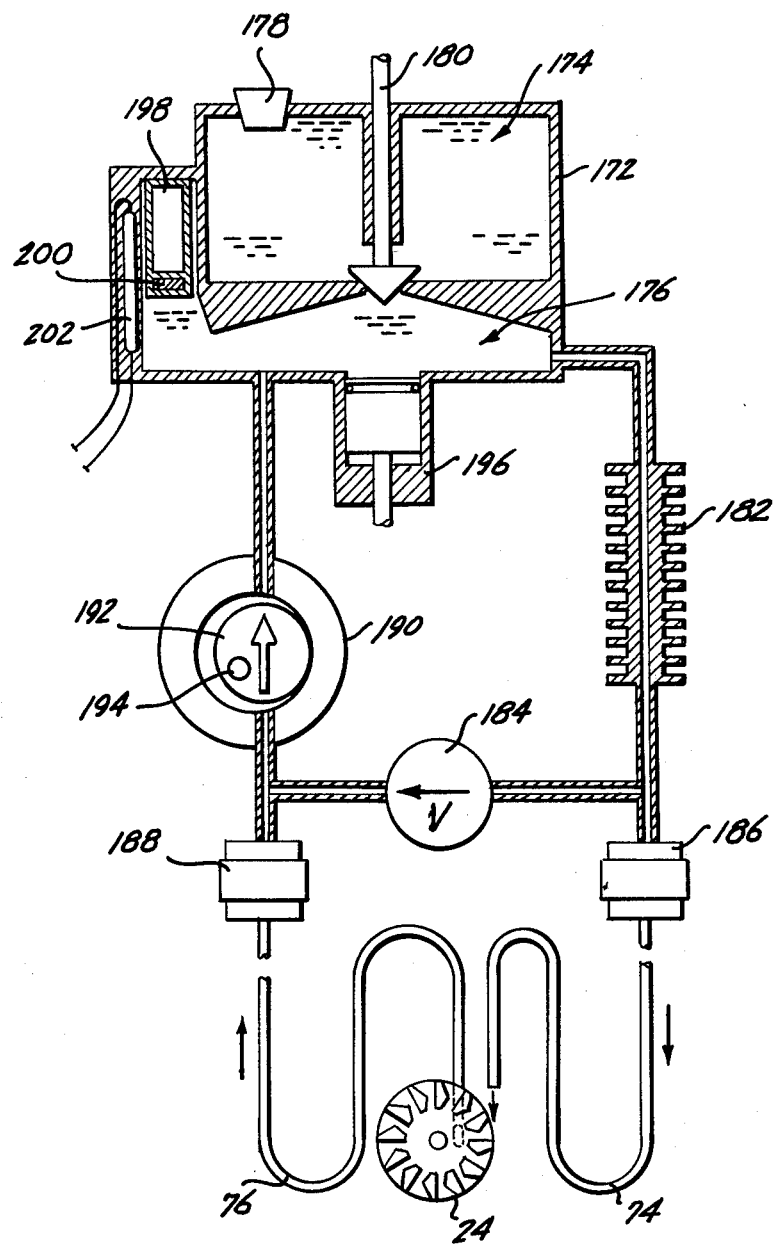
FIG. 8 is a schematic diagram of a fluid drive system for the scan head.

Referring now to the fluid drive system in FIG. 8, the driving and acoustic coupling fluid is contained within a housing 172 having an upper, make-up reservoir 174 and a lower, working reservoir 176. Make-up reservoir 174 is filled with the fluid through a port 178, and working reservoir 176 is supplied with fluid from make-up reservoir 174 through a manually controllable valve 180. During operation of the fluid drive system, valve 180 is closed to accordingly close working reservoir 176 so that the pressure of the fluid therein can be regulated. The fluid is conducted from working reservoir 176 through piping to a heat exchanger 182 and thence through additional piping to a pressure relief valve 184 and a "quick-connect" fluid connector 186. From fluid connector 186, the fluid is conducted to the scan head via flexible fluid inlet tube 74. From the scan head, the fluid is conducted to a "quick-connect" fluid connector 188 through flexible fluid outlet tube 76. Any fluid passing through pressure relief valve 184 and the fluid passing through connector 188 are conducted by piping to the inlet of a pump 190 having an electrical drive motor 192, and the fluid passing through pump 190 is returned by piping to working reservoir 176.

Pump 190 preferably is a gear pump of the type that delivers fluid at a substantially constant pressure at its outlet, which pressure is adjustable by means of an integral pressure adjustment valve 194. This pressure (e.g., 10 psi) is taken to be the nominal working pressure of the fluid drive system; however, the actual working pressure is adjustable within certain limits by a manually controllable or automatic pressure-compensating valve 196 in communication with working reservoir 176. The rate at which fluid recirculates through the fluid drive system and therefore the speed of rotation of rotor 12 are substantially determined by the speed of rotation of pump 190 which in turn is controlled by the speed of rotation of drive motor 192. To provide very accurate and precise control of the speed of rotation of rotor 12 (which may vary from that of pump 190 due to a number of factors including the flexibility of tubes 74 and 76), the speed of rotation of drive motor 192 may be controlled by a phase-lock loop circuit or other servo-control circuit responsive to speed signals obtained through optically encoded ring 26 and one or both of fiber-optic bundles 108 and 110.

Heat exchanger 182 and pressure relief valve 184 provide essentially safety functions in the fluid drive system. That is, heat exchanger 182 minimizes any excessive temperature rise in the recirculating fluid. Fluid connectors 186 and 188 are of the type that inhibit any fluid flow therethrough when disconnected. If fluid connector 186 is disconnected, pressure relief valve 184 (which is normally closed) opens at a predetermined pressure (e.g., 15 psi) above the nominal working pressure of the fluid drive system so as to prevent any damage to the components of the fluid drive, particularly pump 190 and motor 192.

In a scan head of the type shown in the preferred embodiment in which the same fluid is used to both drive the rotor and provide coupling of ultrasonic energy to and from the transducers on the rotor, it is important that the fluid have relatively low attenuation of ultrasonic energy, serve as an excellent lubricant for the rotor bearings and pivots, have a relatively low viscosity so as to not significantly impede rotation of the rotor, and be readily available and replaceable. The fluid having the best combination of these characteristics, and the preferred fluid, is water. A fluid that is generally impractical for use in this type of scan head is air because of its relatively high attenuation of ultrasonic energy. It is therefore desirable that provision be made in the fluid drive system and in the scan head to ensure that air is not present in the fluid recirculated therethrough. In this regard, screw 62 (FIGS. 1 and 2) is rotated until bleed port 64 therein is open and valve 180 is opened. When the resultant head pressure on the fluid has driven all air in the system out through bleed port 64, screw 62 is rotated to close bleed port 64. Since the scan head and fluid drive system will function with air as the fluid, it is desirable that the system be shut down when the desired fluid has reached an abnormally low level. In this regard, a float 198 is disposed within working reservoir 176 and carries a permanent magnet 200. When the desired fluid drops to an abnormally low level, magnet 200 actuates an adjacent reed switch 202 which responsively causes the removal of electrical power from drive motor 192.

From the foregoing description, it will be appreciated that the scan head of the present invention has significant advantages over the scan heads known to the prior art. The provision of a fluid drive and the elimination of an electrical drive for the scan head rotor eliminate the problem of acoustic coupling fluid leakage into the electrical drive motor and the seal required to prevent such leakage, reduce the torque required to drive the rotor, reduce the weight and size of the scan head and the number of movable components therein (only the rotor is movable in the preferred embodiment), reduce the expense of manufacturing and servicing the scan head, provide increased reliability, and permit the scan head to be used in circumstances in which potential electrical or explosive hazards must be eliminated. The elimination of the electrical drive motor and its drive train also makes the scan head almost vibrationless during operation, thereby permitting a fixed Doppler transducer to be mounted on or integral with the scan head. Finally, the structure of the preferred embodiment and the use of the same fluid for both acoustic coupling and rotor drive permit the scan head to be modified or serviced by the user. In this regard, rotor 12 can be easily changed by removing boot 50 and collar 48, separating housing portions 10A and 10B, removing the rotor and inserting a new rotor, reassembling the scan head components, and purging the fluid drive system of air in the manner described.

While the invention has been described with reference to a preferred embodiment, it is to be clearly understood by those skilled in the art that the invention is not limited thereto. As an example, certain of the advantages of the invention can be obtained by using fluid drive for the scan head rotor and by using a separate acoustic coupling fluid for the transducers carried by the rotor. Although such an arrangement will most likely require separate cavities within the scan head in which are disposed the rotor impeller and the rotor transducer portion, with a shaft extending between the impeller and the transducer portion and a seal being provided about the shaft, the problem of fluid leakage between the cavities can be minimized by using the same type of fluid as both the driving fluid and acoustic coupling fluid. In the event that an acceptable seal is provided, even a fluid having a relatively high attenuation of ultrasonic energy (such as air) can be used as the driving fluid. As yet another example, provision may be made so that the rotor can be externally rotated to a desired, fixed angular position so that the transducer may be used to provide a Doppler signal. In this regard, the rotor may be provided at one end (e.g., the end bearing optically encoded ring 26) with ferrous material and an electromagnet may be contained in a rotatable member supported on the scan head housing so that rotation of the external member effects a corresponding rotation of the rotor. Therefore, the scope of the invention is to be interpreted only in conjunction with the appended claims.

The embodiments of the invention in which an exclusive property or privilege is claimed are defined as follows:

1. A rotary ultrasonic scan head comprising:
   a housing;
   a rotor supported within said housing for rotation, said rotor having a predetermined axis of rotation and including at least one ultrasonic transducer that is disposed so as to be capable of ultrasonic energy transmission and reception in directions transverse to said axis of rotation; and,
   a fluid drive motor disposed within said housing and operatively associated with said rotor for rotating said rotor about said axis in response to the supply of a fluid to said fluid drive motor.

2. The scan head of claim 1, further comprising means disposed within said housing and operatively associated with said rotor for coupling electrical signals between said housing and said rotor.

3. The scan head of claim 1, further comprising means disposed within said housing for sensing the relative angular position and speed of rotation of said rotor.

4. The scan head of claim 1, wherein said fluid drive motor includes: a cavity defined within said housing; an impeller disposed within said cavity and forming part of said rotor; and, fluid inlet means and fluid outlet means disposed in said housing and being respectively adapted to conduct fluid to and from said cavity, said fluid inlet means being disposed so as to direct the fluid conducted therethrough at said impeller.

5. The scan head of claim 4, wherein the entirety of said rotor is disposed within said cavity so that the fluid circulated therethrough also serves as an acoustic coupling fluid for the ultrasonic energy transmitted and received by said at least one ultrasonic transducer.

6. The scan head of claim 5, further comprising means disposed in said housing and defining an acoustic window for said cavity for coupling ultrasonic energy between said cavity and the exterior of said housing.

7. The scan head of claim 6, wherein said acoustic window is of flexible material, and further comprising pressure-compensating means disposed within said housing for regulating the pressure of fluid within said cavity upon deflection of said acoustic window.

8. A rotary ultrasonic scan head comprising:
   a housing having a cavity defined therein;
   a rotor disposed within said cavity and supported by said housing for rotation about a predetermined axis, said rotor including: at least one ultrasonic transducer that is disposed so as to be capable of ultrasonic energy transmission and reception in directions transverse to said axis of rotation; and, an impeller composed of a plurality of impeller blades disposed about said axis of rotation; and,
   fluid inlet means and fluid outlet means disposed within said housing and being respectively adapted to conduct fluid to and from said cavity, said fluid inlet means being disposed so as to direct the fluid conducted therethrough at said impeller blades.

9. The scan head of claim 8, further comprising means disposed on said housing and closing said cavity, said means defining therein an acoustic window for coupling ultrasonic energy between said cavity and the exterior of said housing.

10. The scan head of claim 9, wherein said acoustic window is of flexible material, and further comprising a pressure-compensating diaphragm member of flexible material disposed within said housing and closing said cavity.

11. The scan head of claim 8, wherein said housing includes first and second, separable housing portions having corresponding mating surfaces that abut in assembly, and further comprising means for maintaining said first and second housing portions in assembly.

12. The scan head in claim 11, wherein said first and second housing portions are substantially symmetrical and have arcuate peripheral surfaces that form a substantially cylindrical surface in assembly; and wherein said means for maintaining said first and second housing portions in assembly comprises a rotatable collar engageable with said arcuate peripheral surfaces of said first and second housing portions.

13. The scan head of claim 11, wherein said cavity is defined by at least one recess extending into said first housing portion from said mating surface thereof and at least one complementary recess extending into said second housing portion from said mating surface thereof.

14. The scan head of claim 13, wherein said rotor and said recesses are each substantially cylindrical.

15. The scan head of claim 14, wherein each of said recesses is defined by a circumferential sidewall and a floor transverse thereto, and further comprising means mounted in said floor of each said recess and at each end of said rotor for supporting said rotor for rotation upon assembly of said first and second housing portions.

16. The scan head of claim 15, wherein said means for supporting said rotor includes first and second pivots mounted in said floors of said recesses in said first and second housing portions, respectively, and first and second jeweled bearings mounted at the respective ends of said rotor and respectively riding on said first and second pivots.

17. The scan head of claim 15, wherein: said impeller is substantially disposed in assembly within said cylindrical recess in one of said first and second housing portions; said fluid inlet means includes a fluid inlet bore and a nozzle in fluid communication therewith that are disposed in said one of said first and second housing portions, said nozzle being located so as to enter said cylindrical recess in said one of said first and second housing portions through said circumferential sidewall thereof and being disposed so that fluid conducted therethrough exits said nozzle as a jet substantially tangent to said circumferential sidewall; and, said fluid outlet means includes a fluid outlet bore disposed in said one of said first and second housing portions and extending to said floor of said cylindrical recess therein.

18. The scan head of claim 15, wherein said cavity is further defined by a second recess extending into said first housing portion from said mating surface thereof and a complementary second recess extending into said second housing portion from said mating surface thereof, each of said second recesses further extending in directions transverse to said axis of rotation from said circumferential sidewall of said recess in its respective housing portion to an exterior surface of its respective housing portion, said second recesses defining upon assembly of said first and second housing portions an elongated aperture in said exterior surfaces that is transverse to said axis of rotation;

and further comprising a boot removably secured to said first and second housing portions in assembly and closing said elongated aperture, said boot having defined therein an elongated acoustic window that is substantially aligned with said elongated aperture.

19. The scan head of claim 18, wherein: said boot is composed of a flexible material; said cavity is further defined by a third recess extending into said first housing portion from said mating surface thereof and a complementary third recess extending into said second housing portion from said mating surface thereof, said third recesses opposing said second recesses and extending in directions transverse to said axis of rotation and in fluid communication with said cylindrical recesses in said first and second housing portions;

and further comprising a pressure-compensating diaphragm member of flexible material received in said third recesses upon assembly of said first and second housing portions.

20. The scan head of claim 13, wherein said rotor includes plurality of ultrasonic transducers disposed at angular intervals about said axis of rotation, and further comprising means for selectively enabling each said ultrasonic transducer as each said ultrasonic transducer traverses a desired sector.

21. The scan head of claim 20, wherein said means for selectively actuating includes: a plurality of reed switches disposed at angular intervals about said axis of rotation, each reed switch being associated and electrically connected with one of said plurality of ultrasonic transducers and being diametrically opposed to its associated ultrasonic transducer; and, at least one permanent magnet disposed within one of said first and second housing portions in opposition to said desired sector for actuating each said reed switch to enable its associated ultrasonic transducer as its associated ultrasonic transducer traverses said desired sector.

22. The scan head of claim 13, wherein said rotor further includes an optically encoded member that is substantially disposed in assembly within said recess in one of said first and second housing portions; and further comprising means disposed within said one of said first and second housing portions for coupling light to and from said optically encoded member.

23. The scan head of claim 22, wherein said means for coupling light includes: a bore formed in said one of said first and second housing portions and extending to said recess therein; and, a fiber-optic bundle disposed within said bore.

24. The scan head of claim 23, wherein said means for coupling light further includes: a second bore formed in said one of said first and second housing portions and extending to said recess therein, said bore and said second bore being disposed at different angular locations relative to said axis of rotation; and, a second fiber-optic bundle disposed within said second bore.

25. The scan head of claim 13, further comprising a rotary transformer for coupling electrical signals between one of said first and second housing portions and said rotor.

26. The scan head of claim 25, wherein said rotary transformer includes: a first winding disposed within said recess in said one of said first and second housing portions and coaxial with said axis of rotation; and, a second winding carried by said rotor and coaxial with said axis of rotation, said second winding being substantially disposed in assembly in said recess in said one of said first and second housing portions and being aligned with said first winding in directions transverse to said axis of rotation.

27. The scan head of claim 13, further comprising: a bore extending from an exterior surface of one of said first and second housing portions to said recess therein; and, means for selectively closing and opening said bore to permit fluid to be bled from said cavity.

28. In combination with the rotary ultrasonic scan head recited in claim 8, a fluid drive system comprising:
a source of a fluid suitable for rotating said rotor and for coupling ultrasonic energy to and from said at least one ultrasonic transducer included in said rotor; and
means for recirculating said fluid through said source and said scan head, by conducting fluid from said source to said fluid inlet means and by conducting fluid from said fluid outlet means to said source.

29. The combination recited in claim 28, wherein said means for recirculating includes a flexible fluid inlet tube in fluid communication with said fluid inlet means and a flexible fluid outlet tube in fluid communication with said fluid outlet means.

30. The combination of claim 28, wherein said source and said means for recirculating comprise a closed fluid drive system.

31. The combination of claim 30, further comprising means for regulating the pressure of said fluid during recirculation thereof.

32. The combination of claim 30, further comprising means for regulating the speed at which said fluid is recirculated.

33. The combination of claim 28, wherein said fluid is water.

34. The combination of claim 33, wherein said scan head further includes means disposed in said housing for bleeding air from said cavity.

35. A rotor for a rotary ultrasonic scan head, said rotor comprising:
a substantially cylindrical mandrel having a longitudinal axis;
a disc formed at one end of and coaxial with said mandrel;
a bore extending axially through said mandrel and said disc;
a plurality of ultrasonic transducers disposed at angular intervals about said longitudinal axis;

a plurality of reed switches disposed at angular intervals about said longitudinal axis, each said reed switch being associated with one of said plurality of ultrasonic transducers and diametrically opposing its associated ultrasonic transducer;

a printed circuit board affixed in proximity to said disc, said printed circuit board including inner and outer conductive rings each coaxial with said longitudinal axis;

means connecting each reed switch and its associated ultrasonic transducer in electrical circuit with said inner and outer conductive rings;

a winding disposed on said mandrel at its end away from said disc, said winding being coaxial with said longitudinal axis;

means connecting said winding in electrical circuit with said inner and outer conductive rings;

an impeller carried by said mandrel at its end away from said disc, said impeller including a plurality of impeller blades disposed at substantially equal angular intervals about said longitudinal axis, said impeller having a diameter substantially equal to that of said disc;

a body formed about said mandrel intermediate said impeller and said disc, said body being formed from a resinous material that encapsulates said plurality of ultrasonic transducers and said plurality of reed switches; and, a pair of bearings disposed in said bore at opposite ends thereof.

36. A rotor as recited in claim 35, wherein said body is formed by molding said resinous material about said mandrel.

37. A rotor as recited in claim 36, wherein said impeller is also formed by molding said resinous material about said mandrel.

38. A rotor as recited in claim 35, wherein said pair of bearings are jeweled bearings.

39. A rotor as recited in claim 35, further comprising an optically encoded ring carried by said disc, said ring having formed thereon a plurality of areas each having a different light reflectivity from said ring, said plurality of areas being disposed at substantially equal angular intervals about said ring.

40. A rotor as recited in claim 35, further comprising a ferrite slug disposed within said bore and substantially aligned with said winding in directions transverse to said longitudinal axis.

* * * * *